United States Patent
Ammer et al.

(10) Patent No.: US 10,288,629 B1
(45) Date of Patent: May 14, 2019

(54) METHOD OF ASSESSING GROWTH HORMONE DEFICIENCY IN HUMANS BY A MACIMORELIN CONTAINING COMPOSITION

(71) Applicant: AEterna Zentaris, Inc., Charleston, SC (US)

(72) Inventors: Nicola Ammer, Frankfurt (DE); Gilbert Muller, Frankfurt (DE); Richard Sachse, Mittelbiberach (DE); Herbert Sindermann, Norden-Norddeich (DE)

(73) Assignee: Aeterna Zentaris, Inc., Montreal, QC (CA)

( * ) Notice: Subject to any disclaimer, the term of this patent is extended or adjusted under 35 U.S.C. 154(b) by 0 days.

(21) Appl. No.: 15/993,507

(22) Filed: May 30, 2018

Related U.S. Application Data (60) Provisional application No. 62/607,866, filed on Dec. 19, 2017, provisional application No. 62/609,059, filed on Dec. 21, 2017.

(51) Int. Cl.
  *G01N 33/74* (2006.01)
  *G01N 33/49* (2006.01)

(52) U.S. Cl.
  CPC ............ *G01N 33/74* (2013.01); *G01N 33/49* (2013.01); *G01N 2333/61* (2013.01); *G01N 2800/048* (2013.01)

(58) Field of Classification Search
  CPC ........ G01N 33/48; G01N 33/49; G01N 33/68; G01N 33/74; G01N 2800/04; G01N 2800/048; G01N 2800/52; G01N 2333/61; Y10T 436/145555; Y10T 436/17; Y10T 436/200833
  USPC ........... 436/63, 86, 87, 96, 106, 128; 435/29
  See application file for complete search history.

(56) References Cited

U.S. PATENT DOCUMENTS

| | | | |
|---|---|---|---|
| 6,861,409 B2 | 3/2005 | Martinez et al. | |
| 8,192,719 B2 | 6/2012 | Larsen | |
| 9,763,919 B2 * | 9/2017 | Thorner | A61K 31/435 |
| 2010/0216706 A1 * | 8/2010 | Horvath | A61K 38/25 |
| | | | 514/6.9 |

OTHER PUBLICATIONS

Garcia et al. Journal of Clinical Endocrinology & Metabolism, DOI: 10.1210/jc.2018-00665, May 31, 2018.*
Agrawal et al. Expert Reviews Molecular Diagnosis, vol. 14(6), pp. 647-654, 2014.*
Fleseriu, Maria et al., "Hormonal Replacement in Hypopituitarism in Adults: An Endocrine Society Clinical Practice Guideline", *The Journal of Clinical Endocrinology & Metabolism*, vol. 101, Issue 11, Nov. 1, 2016, pp. 3888-3921, https://doi.org/10.1210/jc.2016-2118.
Garcia, JM et al., "Macimorelin (AEZS-130)-Stimulated Growth Hormone (GH) test: Validation of a Novel Oral Stimulation Test for the Diagnosis of Adult GH Deficiency", J Clin Endocrinol Metab. Published online Apr. 4, 2013 as doi:10.1210/jc.2013-1157, 8 pages.
Garcia, JM et al., "Validation of Macimoreline as a Diagnostic Test for Adult Growth Hormone Deficiency (AGHD): A Phase 3 Study in Comparison with the Insulin Tolerance Test (ITT)", Poster, Abstract LB Sun 59, Endocrine Society, Apr. 2, 2017, USA, 1 page.
Yuen, Kevin C.J., "Growth Hormone Stimulation Tests in Assessing Adult Growth Hormone Deficiency," NCBI Bookshelf, A service of the national Library of Medicine, National Institutes of Health, Aug. 1, 2018, Seattle, WA, 15 pages.

* cited by examiner

*Primary Examiner* — Maureen Wallenhorst
(74) *Attorney, Agent, or Firm* — Kilpatrick Townsend & Stockton LLP (57) ABSTRACT

The present invention provides a method for measuring growth hormone level in a human or animal subject, including a method of assessing pituitary-related growth hormone deficiency in a human or animal subject, after macimorelin oral administration to the subject.

13 Claims, 6 Drawing Sheets

Figure 1: Histogram counts for 30 minutes blood draws (time window 25 - 34 minutes)

| 25 | 26 | 27 | 28 | 29  | 30 | 31 | 32 | 33 | 34 |
|----|----|----|----|-----|----|----|----|----|----|
| 1  | 1  | 5  | 5  | 111 | 6  | 2  | 4  | 2  | 2  |

Figure 2: Histogram counts for 45 minutes blood draws (time window 40 – 49 minutes)

| 40 | 41 | 42 | 43 | 44  | 45 | 46 | 47 | 48 | 49 |
|----|----|----|----|-----|----|----|----|----|----|
| 1  | 2  | 2  | 4  | 115 | 6  | 3  | 2  | 2  | 2  |

Figure 3: Histogram counts for 60 minutes blood draws (time window 50 – 69 minutes)

| 50 | 54 | 55 | 56 | 57 | 58 | 59 | 60 | 61 | 62 | 63 | 64 | 65 | 69 |
|---|---|---|---|---|---|---|---|---|---|---|---|---|---|
| 1 | 1 | 0 | 0 | 2 | 1 | 79 | 11 | 16 | 7 | 4 | 14 | 0 | 2 |

Figure 4: Histogram counts for 90 minutes blood draws (84 - 164 minutes)

| 84 | 85 | 86 | 87 | 88 | 89 | 90 | 91 | 92 | 93 | 94 | 95 | 99 | 164 |
|---|---|---|---|---|---|---|---|---|---|---|---|---|---|
| 1 | 2 | 3 | 3 | 6 | 96 | 6 | 2 | 5 | 2 | 9 | 1 | 1 | 1 |

Figure 5: Peak GH concentrations in macimorelin GHST (MAC) and ITT by AGHD likelihood category (N=139)

Figure 6: Scatter plot of peak GH values for core study and reproducibility sub-study (n=33)

METHOD OF ASSESSING GROWTH HORMONE DEFICIENCY IN HUMANS BY A MACIMORELIN CONTAINING COMPOSITION

RELATED APPLICATIONS

This application claims priority to U.S. Provisional Patent Application No. 62/607,866, filed on Dec. 19, 2017, and U.S. Provisional Patent Application No. 62/609,059, filed on Dec. 21, 2017, the contents of which are hereby incorporated by reference in the entirety for all purposes.

BACKGROUND OF THE INVENTION

Growth hormone (GH) is a major body system-wide metabolic hormone that regulates protein, lipid, and carbohydrate homeostasis and is required for growth, development, and maintenance of the body and mind. GH is produced in the anterior lobe of the pituitary gland upon stimulation by growth hormone releasing hormone (GHRH) from the hypothalamus gland. GH is secreted from the pituitary in a pulsatile fashion of approximately 6-10 random bursts during a 24-hour period.

Growth hormone deficiency (GHD) may be classified broadly into four categories based on the source of the GH deficiency: 1) pituitary or "classic" GHD, 2) hypothalamic GHD, 3) functional GHD and 4) idiopathic GHD. Growth Hormone deficiency may become clinically overt in childhood or in the adult. Childhood onset GHD is characterized by short stature, micropenis, increased fat, high-pitched voice, and a propensity to hypoglycemia due to relatively unopposed insulin action. The consequences of GHD in the adult can vary from the inability of young adults to achieve maximum bone density and negative impacts on lean body mass, to cardiovascular risk factors in middle age and to effects on quality of life in older subjects. It is recognized that adult growth hormone deficiency (AGHD) leads to increased morbidity (metabolic syndrome, osteoporosis, muscle wasting impaired quality of life) and increased incidence of cardiovascular events, a main cause of the increased mortality observed in this population. Recombinant human growth hormone was approved in 1996 for the treatment of AGHD. In the USA, it is estimated that the incidence of GHD in children is between 1 in 4,000 and 1 in 10,000. More than 50,000 adults in the US are GHD and 6,000 new cases are reported each year, including GHD children who transition to GHD as an adult (Human Growth Foundation www.hgfound.org).

According to the 2011 Endocrine Society's Clinical Guidelines [Molitch 2011] and other published literature [Woodhouse 1999; Biller 2000; Attanasio 2002; Hoffman 2004; Bollerslev 2006], GH therapy for GHD offers benefits in growth and development in children and in body composition, exercise capacity, endothelial function, inflammatory biomarkers, bone mineral density, and quality of life measures. The diagnosis of GHD is therefore important.

Published guidelines recommend evaluation of AGHD to be based upon clinical findings, medical history, and using the appropriate GH stimulation test (GHST) for biochemical confirmation [Yuen 2011; Yuen 2013]. Since GH is secreted in pulses, random measurements of GH levels (i.e., the blood concentration of GH, expressed e.g. in ng/mL) do not distinguish GH-deficient from GH-sufficient subjects reliably. Accordingly, the diagnosis of AGHD often depends on GHSTs using agents known to provoke endogenous GH release above a certain level in healthy individuals to determine the peak GH level in subjects suspected of having the disorder. Such provocative agents include insulin used in the insulin tolerance test (ITT), arginine+GH releasing hormone (GHRH), arginine alone, clonidine, levodopa and glucagon in the glucagon stimulation test (GST).

The ITT has been considered the gold standard for evaluation of GHD. An intravenous administration of insulin is used to induce hypoglycaemia, which in turn leads to GH release. However, this test is labor intensive as due to the potential risks associated with hypoglycaemia, intensive medical monitoring of the subject is required. The side effects are often reported as dangerous. Furthermore, the ITT is contraindicated in elderly subjects and in subjects with seizure disorders and ischemic heart disease [Yuen 2011; Yuen 2013]. GHRH plus arginine was an alternative to ITT in the USA until 2008 when Geref, the only approved form of GHRH in the USA, was taken off the market.

The GST is an alternative that has grown in usage [Molitch 2011; Yuen 2011; Yuen 2013]. The common side effects of the GST include nausea, vomiting and headaches. Additionally, there are the limitations of the length of the test (3-4 hours) and the need for an intramuscular injection. There remains a real unmet medical need for alternative tests that are safe and reliable.

A test to diagnose GHD based on macimorelin, an orally-available peptidomimetic ghrelin receptor agonist with growth hormone secretagogue (GHS) activity, has been disclosed by Larsen in WO 2007/093820 A1.

Ghrelin potently stimulates GH release [Kojima 1999]. The GH-releasing effects of ghrelin are thought to be mediated by specific receptors mainly present at the pituitary and hypothalamic level [Nogueiras 2006]. In membrane preparations containing the GHS-receptor derived from human hypothalamus and pituitary gland, it was demonstrated that macimorelin shows binding potency to the human GHS receptor comparable to that of its natural ligand, ghrelin [Broglio 2002]. Macimorelin is readily absorbed from the gastrointestinal tract and is assumed to exert its action in the same way as ghrelin.

Based on the ability of macimorelin to exert the release of a GH pulse shortly after oral administration in healthy subjects, macimorelin has been developed as an oral diagnostic agent for GH deficiency in adults.

Macimorelin as a compound and its use in treatment of GHD has been disclosed by Martinez et al. in WO 01/96300 A1.

A poster titled "Validation of Macimorelin As a Diagnostic Test for Adult Growth Hormone Deficiency (AGHD): A Phase 3 Study in Comparison with the Insulin Tolerance test (ITT)" was presented by Garcia et al. on the 99th Annual Meeting of the Endocrine Society in 2017, reporting details of the clinical study.

SUMMARY OF THE INVENTION

The present invention firstly relates to a macimorelin containing composition to diagnose GHD by collecting one or two post-administration samples within a range of 40 to 95 minutes from a subject after oral administration of the macimorelin containing composition.

The composition is comprising macimorelin, lactose monohydrate, crospovidone, silicon dioxide, sodium stearyl fumarate, and saccharin.

In one aspect of the present invention, the GH level of only a single post-administration sample is collected within a range of 40 to 50, 55 to 65 or 85 to 95 minutes after administration for diagnosis of GHD. In another aspect, the peak GH level of two post-administration samples is collected within a range of 40 to 65 minutes after administration or the peak GH level of two post-administration samples is collected within a range of 55 to 95 minutes after administration for diagnosis of GHD.

Secondly, the present invention provides a novel method for measuring growth hormone level in a subject. The method includes these steps: (a) orally administering to the subject an effective amount of macimorelin; and (b) measuring growth hormone level in (i) one blood sample taken from the subject at 60±5 minutes after step (a), or (ii) two blood samples taken from the subject at 45±5 minutes after step (a) and at 60±5 minutes after step (a), or (iii) two blood samples taken from the subject at 60±5 minutes after step (a) and at 90±5 minutes after step (a). Typically, the method does not include any further steps where any additional blood sample is taken from the subject.

In some embodiments, the one or two blood samples are serum samples. In other embodiments, the one or two blood samples are plasma samples. Typically, when two blood samples are taken, they are of the same type: for example, they are two serum samples or two plasma samples. In some embodiments, about 0.5 mg per kg subject bodyweight of macimorelin is orally administered in step (a). In some embodiments, the one blood sample is taken from the subject at 60±5 minutes after step (a). In some embodiments, the two blood samples are taken from the subject at 45±5 minutes after step (a) and at 60±5 minutes after step (a); or the two blood samples are taken from the subject at 60±5 minutes after step (a) and at 90±5 minutes after step (a).

In some embodiments, the growth hormone level measured in the one blood sample in step (b) is compared with a predetermined threshold value, which in some cases is pre-determined, e.g., the predetermined threshold value is 2.8 ng/ml. In some embodiments, the higher growth hormone level measured in the two blood samples in step (b) is compared with a predetermined threshold value, e.g., the predetermined threshold value is 2.8 ng/ml.

In some embodiments, in step (a) the macimorelin is administered in a composition comprising saccharin. For example, the composition may comprise 3.5% macimorelin (calculated as free base), 93.1% spray-dried lactose monohydrate, 2.0% Type A crospovidone, 0.1% colloidal silicon dioxide, 1.0% sodium stearyl fumarate, and 0.3% saccharin sodium dihydrate. In some embodiments, the subject whose growth hormone level is being tested is an adult human or a child. In other cases, the subject whose growth hormone level is being tested is a non-human mammal.

DEFINITIONS

As used herein, a "subject" is a human or a vertebrate animal, especially an animal of a mammalian species, such as a pig, dog, cat, horse/donkey, bull/cow, goat/sheep, rodent, rabbit, fox, etc., and as well as a non-human primate such as a chimpanzee, a monkey, and the like. A "subject" may be of any gender (a male or a female) or age (a juvenile or an adult).

As used herein, the term "effective amount" refers to an amount of a given substance that is sufficient in quantity to produce a desired effect. For example, an effective amount of macimorelin for inducing growth hormone secretion in a recipient is an amount of the compound capable to achieve a detectable increase in the secretion of growth hormone upon its administration to the recipient. Any given amount of macimorelin can be determined by routine testing as to whether or not it is an effective amount for stimulating growth hormone secretion. Typically, an effective amount of macimorelin is in the range of from about 0.01, about 0.02, about 0.05, about 0.10, to about 0.20 mg per kg bodyweight of recipient at the low-end, and from about 1, about 2, about 5, about 10, about 20, about 25, to about 50 mg/kg bodyweight at the high-end, or within a range defined by any one of the low-end amounts and any one of the high-end amounts, e.g., from about 0.20 to about 2 mg/kg body weight, or about 0.5 mg/kg bodyweight.

As used herein, "macimorelin" refers to a peptidomimetic compound acting as the ghrelin receptor agonist with growth hormone secretagogue (GHS) activity. Its chemical structure and use in the treatment of GHD are disclosed in U.S. Pat. No. 6,861,409, WO 01/96300, and WO 2007/093820.

As used herein, the term "blood sample" encompasses a whole blood sample as well as a fraction of whole blood such as serum or plasma sample. Whenever two or more "blood samples" are used for testing in the same method scheme, these "blood samples" are of the same type: for example, if the first sample is serum, then the second and any subsequent samples are also serum.

As used herein, the term "about" denotes a range encompassing minus and plus 10% of a reference value. For example, "about 10" describes a range of 9 to 11.

All patents, patent applications, and other publications, including GenBank Accession Numbers, cited in this application are incorporated by reference in the entirety for all purposes.

DETAILED DESCRIPTION OF THE INVENTION

In general, samples are collected from a subject undergoing a GHST to determine GH levels after administration of a provocative agent inducing GH secretion. The number of samples to be collected and the test duration are important parameters to describe the subject's burden during the test as well as to describe the effort of the healthcare professional (HCP) conducting the test. The lower the number of samples is and/or the shorter a test duration is, the higher will be the acceptance to conduct such a test for subject and HCP. This is in particular true, when the subject is a child.

The following table 1 summarizes the total number of collected blood samples during a GHST administered via injection, as recommended by the Endocrine Society and the American Association of Clinical Endocrinologists (AACE).

TABLE 1

Total number collected blood samples during a GHST administered via injection

| Test | RoA | Recommended by | Time of Blood samples collected after administration. | Sample # | Time of Test |
|---|---|---|---|---|---|
| Insulin (ITT) | IV | Endo | −30, 0, 30, 60 and 120 minutes [a)] | 5 | 3 hours |
|  |  | AACE | fasting, and 20, 30, 40, and 60 min after a hypoglycemia is achieved. [b)] | 5 | 3 hours |
| Glucagon (GST) | IM | Endo | 0, 30, 60, 90, 120, 150, 180, 210, and 240 min [a)] | 9 | 4 hours |
|  |  | AACE | 0, 30, 60, 90, 120, 150, 180, 210 and 240 minutes [b)] | 9 | 4 hours |
| Arginine | IV | Endo | — | — | — |
|  |  | AACE | −30, 0, 30, 60, 90, 120, 150 minutes [a)] | 7 | 3 hours |
| GHRH + Arg | IV | Endo | 0, 30, 45, 60, 75, 90, 105, and 120 minutes [b)] | 7 | 3 hours |
|  |  | AACE | −30, 0, 30, 60, 90, 120 and 150 minutes [d)] | 7 | 3 hours |

RoA: Route of Administration, Sample #: number of collected samples
[a)] M. Fleseriu, J Clin Endcrinol Met, 2016, 3888 - 3921
[b)] K. Yuen, Endocr Pract, 2016, 1235-1244

It is clearly visible that all GHSTs administered via injection collect at least 5 samples during a time window of at least 120 min, including at least one pre-dose sample, i.e., at 0 minutes and/or before. Therefore, it can be concluded that a full GH level profile including pre-administration level(s) is a clinical standard.

This standard exits for several years. In 1998, Davies described the ITT collecting blood sample at 0, 30, 60, 90, and 120 minutes. In 2002, Gomez described the GST collecting blood samples at baseline, 90, 120, 150, 180, 210 and 240 minutes. In a study comparing 6 GHSTs in 2002, Biller collected 6 blood samples within −30 to 150 minutes (Biller, B. M. K. et al., J. Clin. Endocrinol. Metab. (2002), 87(5), p 2067-2079).

It should be noted that despite proposals to use a smaller number of blood samples (e.g. Jabbar et al., Scand. J. Clin. Lab. Invest, 2009, 359-64, or Aimaretti et al., Pituitary, 2001, 129-34), two major associations of clinical endocrinologists recommended collection of full GH profiles as recently as 2016 (see Table 1). This may be due to the burden of a GHST on the subject. A high number of blood samples will prevent repetition of a GHST should an error during blood sampling or GH determination invalidates use of a blood sample.

The macimorelin based test disclosed by Larsen in WO 2007/093820 A1 is the only orally administered GHST so far.

Claim 1 of WO 2007/093820 A1 is directed to:

1. A method of assessing growth hormone deficiency in a human or animal subject, the method comprising administering orally to the subject EP 1572 [i.e., macimorelin] or EP 1573, obtaining at least one post-administration sample from the subject, determining the level of growth hormone in sample or samples and assessing whether the level of growth hormone in the sample or samples is indicative of growth hormone deficiency in the subject.

Further disclosed is a composition containing macimorelin, lactose monohydrate, crospovidone, silicon dioxide, and sodium stearyl fumarate for oral administration.

The number of needed samples are mentioned to be "at least one post-administration sample" (claim 1) or "two or three or four or five samples" (p. 7, line 25).

However, apart from such rather general statements, WO 2007/093820 A1 is silent regarding the specific number of samples or the corresponding time points. In addition, there is no reason given why a smaller number of samples should be sufficient compared to the clinical standard of a full GH level profile.

While being silent on the specific number of the "at least one post-administration sample", WO 2007/093820 A1 discloses the sampling of full GH level profiles, as presented in Example 1 disclosing a macimorelin based GHST with one pre-dose and 11 post-dose samples ranging from a pre-dose to a 300-minute sample (p. 16 line 8), Example 2 disclosing a macimorelin based GHST with one pre-dose and 6 post-dose samples ranging from a pre-dose to a 150-minute sample (p. 18, lines 5-6) and Example 3 disclosing a macimorelin based GHST with one pre-dose and 5 post-dose samples ranging from a pre-dose sample to a 120-minute sample (p. 18, lines 25-28). Example 3 is marked as a "Standard protocol".

In consequence, a person skilled in the art will conclude that only full GH level profile are disclosed by Larsen, being in alignment with the clinical standard known from the prior art. There is no teaching nor any guidance whether the pre-dose sample can be omitted nor whether any sample number lower than 5 appears suitable, or which time point should be chosen to collect the "at least one post-administration sample".

It has now surprisingly been found that pituitary-related growth hormone deficiency is diagnosed in a human or animal subject, when after oral administration of a macimorelin containing composition to said subject a single or two post-administration samples within a range of 40 to 95 minutes after administration are collected from said subject, the level of growth hormone in the single sample or the two samples is determined and found to be below 2.8 ng/ml. The macimorelin containing composition comprises of macimorelin, lactose, crospovidone, silicon dioxide, stearyl fumarate, and saccharin.

Typically, a test to diagnose GHD using a macimorelin containing composition (further referred to as "macimorelin test") is conducted by a healthcare professional (HCP) in a medical setting, e.g. in a medical practice or a clinic or hospital. The HCP prescribes the macimorelin test after an initial assessment that the subject exhibits risk factors for GHD and therefore requires a GHST to confirm a GHD diagnose. There are no contraindications known that prevent the use of a macimorelin containing composition in a subject.

The HCP assures that the subject is fasted for 6-8 hours before the macimorelin test. Typically, the HCP uses a macimorelin test kit comprising the macimorelin containing composition provided in a single use container and prepares a 0.5 mg per mL macimorelin solution according to the instructions included in the kit. Then the HCP determines the individual quantity of the solution based on the subject's weight and have the subject drink the individual quantity.

After administration of the macimorelin solution, the subject waits for 40 to 95 minutes and one or two samples are collected from the subject within that time window. There is no sample taken before administration of the macimorelin solution (no pre-dose sample). As the macimorelin test is safe and generally very well tolerated, there are no severe adverse reactions to be expected, based on the macimorelin safety profile established during clinical studies. Constant medical supervision is not required. Mild to moderate adverse reactions might occur as dysgeusia (4.5%), dizziness, headache, fatigue (each 3.9%), nausea, and hunger (each 3.2%), diarrhea, upper respiratory tract infection (each 1.9%), feeling hot, hyperhidrosis, nasopharyngitis, and sinus bradycardia (each 1.3%).

The level of blood growth hormone is measured using a suitable GH assay, e. g. using an automated chemiluminescence immunoassay.

The determined GH level induced by macimorelin is assessed to diagnose GHD by using a cut-off value of 2.8 ng/mL. A determined GH level below the cut-off value is indicative of having GHD.

In one aspect of the invention, the single post-administration sample is collected from the subject within 40 to 50 minutes after administration, i.e. within a time window of 5 minutes before and after 45 minutes after administration, or in other words, within 45±5 minutes after administration.

In one aspect of the invention, the single post-administration sample is collected from the subject within 55 to 65 minutes after administration, i.e. within a time window of 5 minutes before and after 60 minutes after administration, or in other words, within 60±5 minutes after administration.

In one aspect of the invention, the single post-administration sample is collected from the subject within 85 to 95 minutes after administration, i.e. within a time window of 5 minutes before and after 90 minutes after administration, or in other words, within 90±5 minutes after administration.

In another aspect, the two post-administration samples are collected from the subject within 40 to 65 minutes after administration. Preferably, the first of the two post-administration samples is collected from the subject within 40 to 50 minutes and the second within 55 to 65 minutes after administration, i.e. the first sample is collected within a time window of 5 minutes before and after 45 minutes after administration, or in other words, within 45±5 minutes after administration and the second sample is collected within a time window of 5 minutes before and after 60 minutes after administration, i.e. within 55 to 65 minutes after administration, or in other words, within 60±5 minutes after administration. The highest GH level ("peak level") of said two samples is used to diagnose GHD.

In another aspect, the two post-administration samples are collected from the subject within 55 to 95 minutes after administration. Preferably, the first of the two post-administration samples is collected from the subject within 55 to 65 minutes and the second within 85 to 95 minutes after administration, i.e. the first sample is collected within a time window of 5 minutes before and after 60 minutes after administration, or in other words, within 60±5 minutes after administration and the second sample is collected within a time window of 5 minutes before and after 90 minutes after administration, i.e. within 85 to 95 minutes after administration, or in other words, within 90±5 minutes after administration. The highest GH level ("peak level") of said two samples is used to diagnose GHD.

In yet another aspect of the invention, said human or animal subject to be diagnosed may be either a child or an adult. Examples for an animal subject include a horse, cow, sheep, pig, goat, cat, or dog.

In yet another aspect of the invention, said single post-administration sample to be collected from the subject is a blood sample, a serum sample, or a plasma sample. Said two post-administration samples are two blood samples, two serum samples or two plasma samples, as needed.

EXAMPLES

Example 1: A Macimorelin Containing Composition for Diagnosing GHD

The macimorelin containing composition comprises the following ingredients as listed in Table 2.

TABLE 2

| Composition per unit dose | | |
|---|---|---|
| Composition | Unit quantity | Percentage Quantity |
| Macimorelin (content = 100%) | 0.0350 g | 3.50% |
| Lactose monohydrate, spray-dried | 0.9310 g | 93.10% |
| Crospovidone, Type A | 0.0200 g | 2.00% |
| Colloidal silicon dioxide | 0.0010 g | 0.10% |
| Sodium stearyl fumarate | 0.0100 g | 1.00% |
| Saccharin sodium, dihydrate | 0.0030 g | 0.30% |
| Total | 1.0000 g | 100.00% |

One unit dose consists of 1.000 g macimorelin containing composition for preparation of an oral solution in water. Typically, the prepared solution contains 0.5 mg macimorelin per ml solution.

A bodyweight adjusted aliquot of the reconstituted solution is administered to the subject resulting in a dose of 0.5 mg per kilogram body weight of the subject.

Said unit dose is defined for a macimorelin calculated as a free base with a content of 100%. The mass of the macimorelin free base or its free base equivalent within said unit dose is adjusted according to the content.

Macimorelin can be included in said unit dose as a suitable pharmaceutical salt. Examples for suitable pharmaceutical salts are the acetate salt and the trifluoro acetate salt.

Said unit dose might be filled into a suitable container for easy availability of the GHD test. Examples for a suitable container are a sachet or a pouch, or containers of suitable size made of glass of plastic.

Based on the unit dose and the recommended dose of 0.5 mg per kilogram body weight of the subject, several amounts of macimorelin containing composition may be provided per container.

For a subject of up to 120 kg, the container with macimorelin containing composition may comprise 63.6 mg macimorelin, 1691.8 mg spray-dried lactose monohydrate, 36.6 mg Type A crospovidone, 1.8 mg colloidal silicon dioxide, 18.2 mg sodium stearyl fumarate, and 5.5 mg saccharin sodium dihydrate. When reconstituted in 120 mL of water, 1 mL provides 0.5 mg macimorelin.

If needed, the container may be filled with a small amount of macimorelin containing composition in addition to said unit dose ("overfill"). Such an overfill ensures that the concentration of the macimorelin solution is 0.5 mg/mL despite a small amount of composition remaining in the container due to for example absorption effects. The amount of overfill depends on the type of container and must be determined empirically.

For a sachet made of polyethylene-laminated aluminum foil intended for subjects up to 120 kg, the overfill is 3.6 mg.

Example 2: Use of Saccharin in the Macimorelin Containing Composition to Mask Bad Taste In a multicenter, randomized, two-way, crossover study, 100 subjects with confirmed AGHD received GHRH+L-Arg and macimorelin as GHSTs to determine the diagnostic efficacy of macimorelin for AGHD [Garcia 2013].

This study was conducted in two parts. In the first part, the macimorelin containing composition described in Example 1, but without saccharin was used and mild to moderate bad taste was reported by 12 out of 52 (21%) subjects.

During a study halt, saccharin was found to be a suitable taste masking agent, although the bitter taste was still not fully masked. In the second part of the study, the macimorelin containing composition described in Example 1 (with saccharin) was used, and only 1 out of 48 (2%) test subjects reported bad taste in mild intensity.

Example 3: Comparing the Diagnostic Performance of Macimorelin to the ITT for the Diagnosis of AGHD In a multicenter, open-label, randomized, 2-way crossover clinical trial, 157 subjects received at least one dose of macimorelin (using the macimorelin containing composition as described in Example 1) or the ITT and were included into the safety data set. Of these, 139 subjects with a valid macimorelin test and a valid ITT were included into the efficacy data set, stratified into high (Group A, n=38), intermediate (Group B, n=37), and low (Group C, n=39) likelihood for AGHD and healthy, matched controls (Group D, n=25).

Blood Sample Collection

Blood samples were collected before and 30, 45, 60, and 90 minutes after administration of macimorelin and before and 15, 30, 45, 60, 90 and 120 minutes after administration of insulin to the efficacy data set subjects and GH levels were determined for all samples.

The study protocol allowed for a 5 minutes time window for each of said time points, meaning that a blood sample collected for example within 25 to 35 min after GH provocation agent administration was validly collected for the 30 min time point.

The distribution of collected blood draws per timepoint following administration of macimorelin is shown in the table 3 and FIGS. 1-4 below.

TABLE 3

Overview of statistical data on time distribution following administration of macimorelin

| Time.Point | N | Mean | StDev | Median | Min | Max |
|---|---|---|---|---|---|---|
| 30 min | 139 | 30.122 | 1.17 | 30 | 25 | 35 |
| 45 min | 139 | 45.122 | 1.113 | 45 | 40 | 50 |
| 60 min | 138 | 61.087 | 2.297 | 60 | 50 | 70 |
| 90 min | 138 | 90.978 | 6.644 | 90 | 85 | 165 |

Agreement of the Macimorelin GHST with the ITT

Using GH cut-off levels of 2.8 ng/mL for macimorelin and 5.1 ng/mL for the ITT, percent agreements between the Macimorelin and the ITT GHST were found as listed in Table 4. A GH level below 2.8 ng/mL for macimorelin and 5.1 ng/mL for the ITT is referred to as a positive test, suggesting AGHD.

TABLE 4

Agreement of the Macimorelin GHST with the ITT (N = 139)

| | [minutes] | | | | | | |
|---|---|---|---|---|---|---|---|
| peak of 0-90 | pre-dose | 30 | 45 | peak of 45 & 60 | 60 | peak of 60 & 90 | 90 |
| Negative % agreement | 95.38 | 13.85 | 73.85 | 86.15 | 95.38 | 95.31 | 95.38 | 84.62 |
| Positive % agreement | 74.32 | 98.65 | 82.43 | 78.38 | 75.68 | 81.08 | 78.38 | 86.49 |
| Total % agreement | 84.17 | 58.99 | 78.42 | 82.01 | 84.89 | 87.68 | 86.33 | 85.61 |

When assessing the highest GH level determined over all Macimorelin samples and comparing to the highest GH level determined over all ITT samples, 95.38% of negative Macimorelin test results matched negative ITT test results. Similarly, 74.32% of positive Macimorelin test results matched positive ITT test results, resulting in a total agreement of 84.17% between the macimorelin and the ITT GHST.

When taking only the 45 min macimorelin GH level to compare to the highest GH level determined over all ITT samples, negative agreement is 86.15%, positive agreement is 78.38% and total agreement is 82.01% between the macimorelin and the ITT GHST.

When taking the peak macimorelin GH level for 45 and 60 min to compare to the highest GH level determined over all ITT samples, negative agreement is 95.38%, positive agreement is 75.68% and total agreement is 84.89% between the macimorelin and the ITT GHST.

A negative % agreement value (i.e., a negative macimorelin GHD diagnosis matching a negative ITT GHD diagnosis) is considered as more important compared to the positive % agreement, because a chronic treatment of a subject, who does not need such treatment, based on a false-positive GHST result should be avoided. Nevertheless, a high positive % agreement is also sought. However, criteria for positive agreement might be less stringent as a HCP will base a diagnosis on the overall clinical presentation guided by physical examination, medical history, clinical symptoms, concomitant risk factors and laboratory parameters of a subject, not only on a GHST.

Peak GH Response in the Macimorelin GHST and ITT

Figure 1:
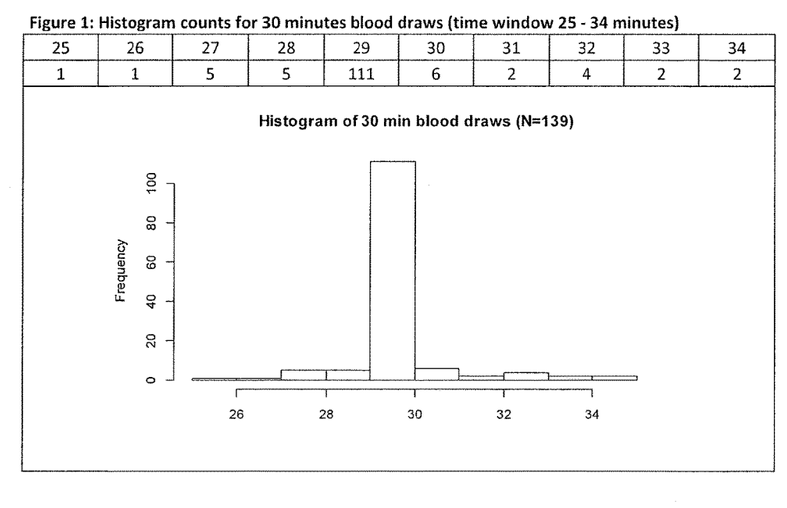
FIG. 1: Histogram counts for 30 minutes blood draws (time window 25-34 minutes).
Figure 2:
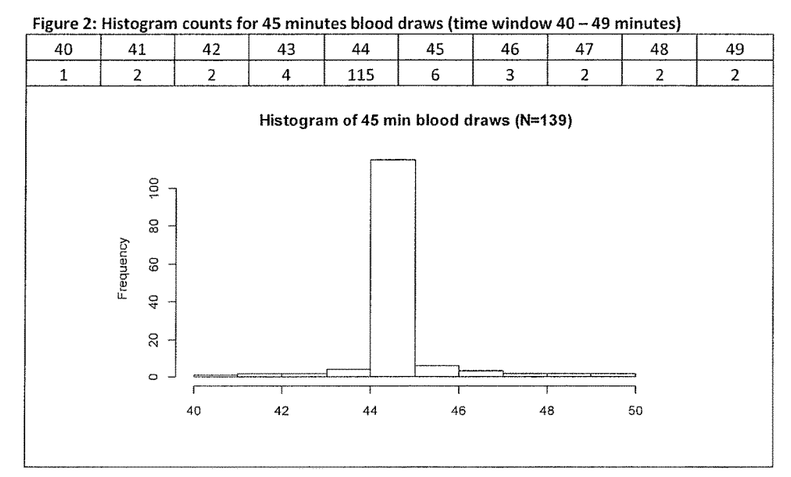
FIG. 2: Histogram counts for 45 minutes blood draws (time window 40-49 minutes).
Figure 3:
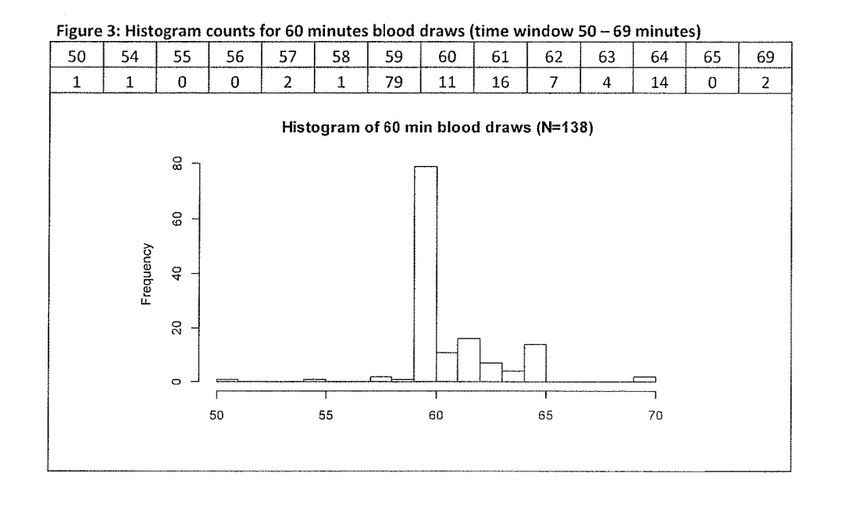
FIG. 3: Histogram counts for 60 minutes blood draws (time window 50-69 minutes).
Figure 4:
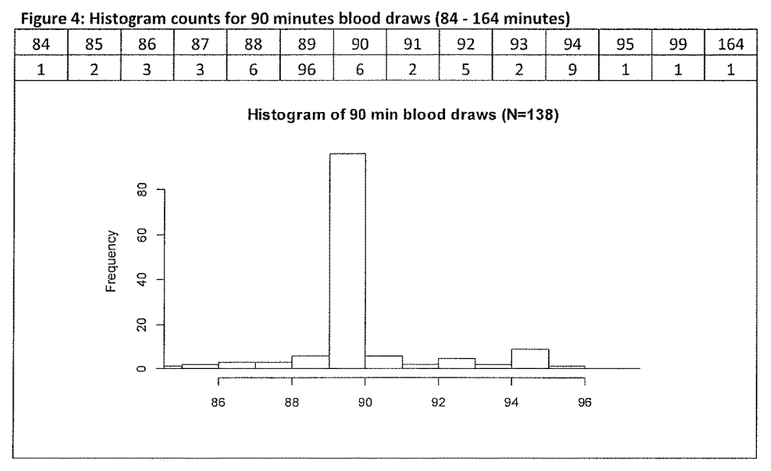
FIG. 4: Histogram counts for 90 minutes blood draws (84-164 minutes).
Figure 5:
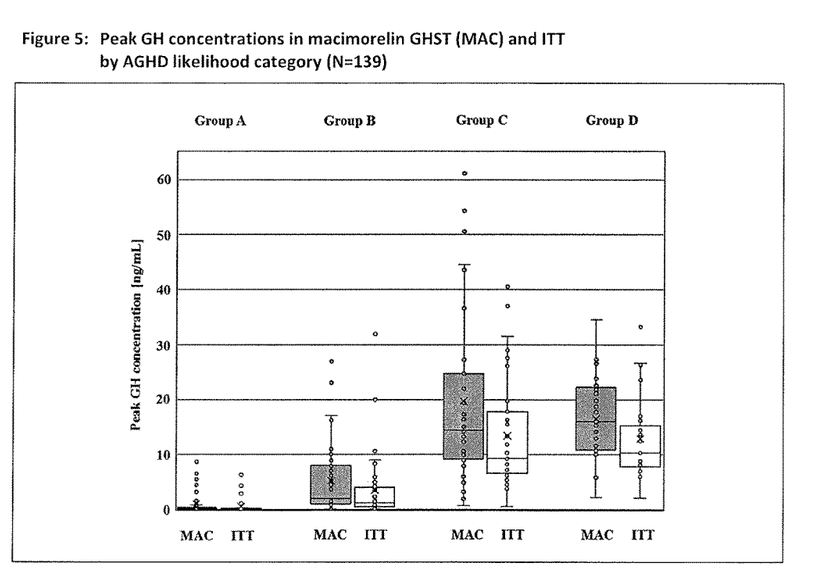
FIG. 5: Peak GH concentrations in macimorelin GHST (MAC) and ITT by AGHD likelihood category (N=139).

The box-plot in FIG. 5 summarizes by AGHD likelihood group the peak GH concentrations achieved in the macimorelin GHST and in the ITT. It is evident that higher peak GH levels in the macimorelin GHST, as compared to the ITT, are consistently seen in all groups of the study. Moreover, the data show that peak GH levels were inversely related to the likelihood of having AGHD, i.e., the subjects assigned to the intermediate likelihood (Group B) had lower GH levels than subjects assigned to the low likelihood (Group C).

Repeatability of the Macimorelin GHST

Figure 6:
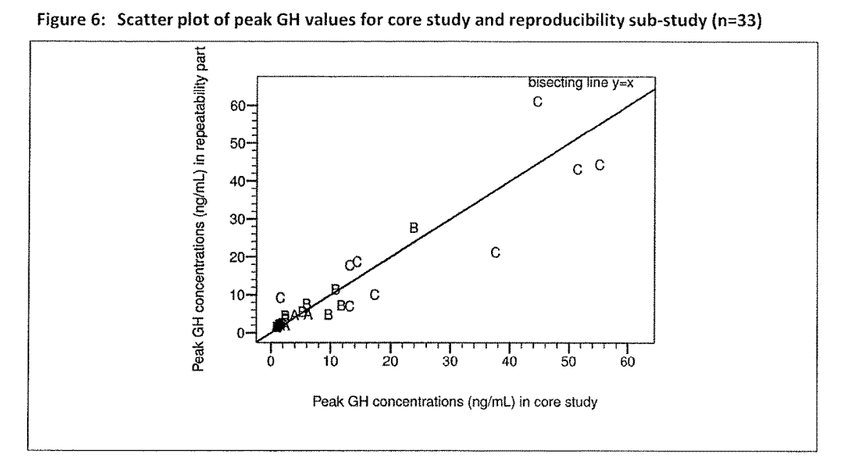
FIG. 6: Scatter plot of peak GH values for core study and reproducibility sub-study (n=33).

To assess the repeatability of the macimorelin GHST, 33 subjects with a valid first macimorelin test (core study) underwent a second macimorelin test (repeatability study extension). The result of the second macimorelin test matched the result of the first test in 94%., i.e., in 31 out of 33 subjects the outcome of the test results below or above the cut-off point was reproducible (FIG. 6).

Common Adverse Reactions after Administration of Macimorelin

Any test emergent adverse event (TEAE) was recorded in 39 (25.3%) of a total of 154 subjects of the safety set following the macimorelin GHST and in 151 (96.2%) of a total of 157 subjects following ITT, with a total number of 77 and 761 AEs, respectively (Table 5).

Severe TEAEs after the ITT included in the order of decreasing frequency: 5 (3.2%) subjects each with somnolence, hyperhidrosis; 4 (2.5%) with asthenia; 3 (1.9%) with hunger; 2 (1.3%) with nervousness, and 1 (0.6%) with tremor. TEAEs following macimorelin GHST were of mild to moderate intensity: dysgeusia (4.5%), dizziness, headache, fatigue (each 3.9%), nausea, hunger (each 3.2%), diarrhea, upper respiratory tract infection (each 1.9%), feeling hot, hyperhidrosis, nasopharyngitis, and sinus bradycardia (each 1.3%).

TABLE 5

Common Adverse Reactions after administration of macimorelin

| | Macimorelin GHST (N = 154/33) | | | ITT (N = 157) | | |
|---|---|---|---|---|---|---|
| TEAEs | Frequency[1] *A/**B | %[2] *A/**B | N AEs[3] *A/**B | Frequency[1] | %[2] | N AEs[3] |
| Any TEAE | 39/6 | 25.3/17.6 | 77/9 | 151 | 96.2 | 761 |
| Any TEAE (likely or possible related) | 22/4 | 14.3/11.8 | 37/5 | 149 | 94.9 | 710 |
| Any test emergent severe AE | 1/0 | 0.6/0 | 1/0 | 11 | 7 | 25 |

[1]Number of subjects with any TEAE, each subject was counted only once within each category,
[2]Number of subjects with any AE/number of all subjects,
[3]Number of all AEs,
*A: All subjects with at least one macimorelin GHST;
**B: Repeatability macimorelin GHST

| List of References | |
|---|---|
| Molitch 2011 | Molitch ME, Clemmons DR, Malozowski S, Merriam GR, Vance ML. Evaluation and treatment of adult growth hormone deficiency: an Endocrine Society clinical practice guideline. J Clin Endocrinol Metab 2011;96(6):1587-609 |
| Woodhouse 1999 | Woodhouse LJ, Asa SL, Thomas SG, Ezzat S. Measures of submaximal aerobic performance evaluate and predict functional response to growth hormone (GH) treatment in GH-deficient adults. J Clin Endocrinol Metab 1999;84:4570-7 |
| Biller 2000 | Biller BM, Sesmilo G, Baum HB, Hayden D, Schoenfeld D, Klibanski A. Withdrawal of long-term physiological growth hormone (GH) administration: differential effects on bone density and body composition in men with adult-onset GH deficiency. J Clin Endocrinol Metab 2000;85:970-6 |
| Attanasio 2002 | Attanasio AF, Howell S, Bates PC, Frewer P, Chipman J, Blum WF, Shalet SM. Body composition, IGF-I and IGFBP-3 concentrations as outcome |

| | List of References |
|---|---|
| | measures in severely GH-deficient (GHD) patients after childhood GH treatment: a comparison with adult onset GHD patients. J Clin Endocrinol Metab 2002;87:3368-72 |
| Hoffman 2004 | Hoffman AR, Kuntze JE, Baptista J, Baum HB, Baumann GP, Biller BM, Clark RV, Cook D, Inzucchi SE, Kleinberg D, Klibanski A, Phillips LS, Ridgway EC, Robbins RJ, Schlechte J, Sharma M, Thorner MO, Vance ML. Growth hormone (GH) replacement therapy in adult-onset gh deficiency: effects on body composition in men and women in a double-blind, randomized, placebo-controlled trial. J Clin Endocrinol Metab 2004;89:2048-56 |
| Boilerslev 2006 | Boilerslev J, Ueland T, Jorgensen AP, Fougner KJ, Wergeland R, Schreiner T, Burman P. Positive effects of a physiological dose of GH on markers of atherogenesis: a placebo-controlled study in patients with adult-onset GH deficiency. Eur J Endocrinol 2006;154:537-43 |
| Yuen 2011 | Yuen KC. Glucagon stimulation testing in assessing for adult growth hormone deficiency: current status and future perspectives. ISRN Endocrinol 2011; article ID 608056 |
| Yuen 2013 | Yuen KCJ, Chong LE, Rhoads SA. Evaluation of adult growth hormone deficiency: current and future perspectives. 2013 Feb 28. In: De Groot LJ, Chrousos G, Dungan K, Feingold KR, Grossman A, Hershman JM, Koch C, Korbonits M, McLachlan R, New M, Purnell J, Rebar R, Singer F, Vinik A, editors. Endotext [Internet]. South Dartmouth (MA): MDText.com, Inc.; 2000-. Available from http://www.ncbi.nlm.nih.gov/books/NBK278928/ |
| Kojima 1999 | Kojima M, Hosoda H, Date Y, Nakazato M, Matsuo H, Kangawa K. Ghrelin is a growth-hormone-releasing acylated peptide from stomach. Nature 1999;402(6762):656-60 |
| Nogueiras 2006 | Nogueiras R, Perez-Tilve D, Wortley KE, Tschöp M. Growth hormone secretagogue (ghrelin-) receptors--a complex drug target for the regulation of body weight. CNS Neurol Disord Drug Targets 2006;5(3):335-43 |
| Broglio 2002 | Broglio F, Boutignon F, Benso A, Gottero C, Prodam F, Arvat E, Ghè C, Catapano F, Torsello A, Locatelli V, Muccioli G, Boeglin D, Guerlavais V, Fehrentz JA, Martinez J, Ghigo E, Deghenghi R.EP1572: A novel peptido-mimetic GH secretagogue with potent and selective GH-releasing activity in man. J Endocrinol Invest. 2002 Sep;25(8):RC26-8. |
| Martinez et al. | U.S. Pat. No. 6,861,409 |
| Martinez et al. | WO 01/96300 A1 |
| Poster by Garcia et al. | "Validation of Macimorelin As a Diagnostic Test for Adult Growth Hormone Deficiency (AGHD): A Phase 3 Study in Comparison with the Insulin Tolerance test (ITT)", presented on the 99th Annual Meeting of the Endocrine Society in 2017 |
| Garcia 2013 | Macimorelin (AEZS-130)-Stimulated Growth Hormone (GH) test: Validation of a Novel Oral Stimulation Test for the Diagnosis of Adult GH Deficiency; J Clin Endocrinol Metab. 2013 Jun;98(6):2422-9 |
| Fleseriu 2016 | M. Fleseriu et al: Hormonal Replacement in Hypopituitarism in Adults: An Endocrine Society Clinical Practice Guideline; J Clin Endcrinol Met, 2016, 3888-3921 |
| Yuen 2016 | K. Yuen et al.: Growth hormone Stimulation Tests in Assessing Adult Growth Hormone Deficiency; Endocr Pract, 2016, 1235-1244 |
| Davies 1998 | Clin Endocrinol (Oxf). 1998, 217-20. |
| Gomez 2002 | Clinical Endocrinology (2002), 56, 329-334 |
| Biller 2002 | Biller, B. M. K. et al., J. Clin. Endocrinol. Metab. (2002), 87(5), p 2067-2079 |
| Jabbar 2009 | Jabbar et al., Scand. J . Clin. Lab. Invest, 2009, 359-64 |
| Aimaretti 2001 | Aimaretti et al., Pituitary, 2001, 129-34 |
| Larsen | WO 2007/093820 A1 |

What is claimed is:

1. A method for measuring growth hormone level in a subject, comprising:
   (a) orally administering to the subject an amount of macimorelin effective for inducing growth hormone secretion;
   (b) measuring growth hormone level in (i) one blood sample taken from the subject at 60±5 minutes after step (a), or (ii) two blood samples taken from the subject at 45±5 minutes after step (a) and at 60±5 minutes after step (a), or (iii) two blood samples taken from the subject at 60±5 minutes after step (a) and at 90±5 minutes after step (a), and wherein no additional blood sample is taken from the subject;
   (c) comparing (i) the growth hormone level in the one blood sample taken from the subject at 60±5 minutes after step (a), or (ii) the growth hormone levels in the two blood samples taken from the subject at 45±5 minutes after step (a) and at 60±5 minutes after step (a), or (iii) the growth hormone levels in the two blood samples taken from the subject at 60±5 minutes after step (a) and at 90±5 minutes after step (a) with threshold value 2.8 ng/ml; and
   (d) determining the subject, whose growth hormone level in the one blood sample in (i) is lower than 2.8 ng/ml or whose growth hormone levels in the two blood samples in (ii) or (iii) are both lower than 2.8 ng/ml, as having growth hormone deficiency, and determining the subject, whose growth hormone level in the one blood sample in (i) is no lower than 2.8 ng/ml or whose at least one of the growth hormone levels in the two blood samples in (ii) or (iii) is no lower than 2.8 ng/ml, as having no growth hormone deficiency.

2. The method of claim 1, wherein the one or two blood samples are serum samples.

3. The method of claim 1, wherein the one or two blood samples are plasma samples.

4. The method of claim 1, wherein about 0.5 mg per kg subject bodyweight of macimorelin is orally administered in step (a).

5. The method of claim 1, wherein the one blood sample is taken from the subject at 60±5 minutes after step (a).

6. The method of claim 1, wherein the two blood samples are taken from the subject at 45±5 minutes after step (a) and at 60±5 minutes after step (a).

7. The method of claim 1, wherein the two blood samples are taken from the subject at 60±5 minutes after step (a) and at 90±5 minutes after step (a).

8. The method of claim 1, wherein in step (a) the macimorelin is administered in a composition comprising saccharin.

9. The method of claim 8, wherein the composition comprises 3.5% w/w macimorelin (calculated as free base), 93.1% w/w spray-dried lactose monohydrate, 2.0% w/w Type A crospovidone, 0.1% w/w colloidal silicon dioxide, 1.0% w/w sodium stearyl fumarate, and 0.3% w/w saccharin sodium dihydrate.

10. The method of claim 1, wherein the subject is an adult human.

11. The method of claim 1, wherein the subject is a human child.

12. The method of claim 1, wherein the subject is a non-human mammal.

13. The method of claim 1, wherein in step (b) growth hormone level is measured in (i) one blood sample taken from the subject at 60±5 minutes after step (a), or (ii) two blood samples taken from the subject at 60±5 minutes after step (a) and at 90±5 minutes after step (a).

* * * * *